United States Patent
Lalgudi

(10) Patent No.: US 10,889,693 B2
(45) Date of Patent: Jan. 12, 2021

(54) EMULSIFIED OILS

(71) Applicant: Ohio Soybean Council, Worthington, OH (US)

(72) Inventor: Ramanathan S. Lalgudi, Westerville, OH (US)

(73) Assignee: Ohio Soybean Council, Worthington, OH (US)

( * ) Notice: Subject to any disclaimer, the term of this patent is extended or adjusted under 35 U.S.C. 154(b) by 0 days.

(21) Appl. No.: 16/059,936

(22) Filed: Aug. 9, 2018

(65) Prior Publication Data

US 2019/0048148 A1 Feb. 14, 2019

Related U.S. Application Data

(60) Provisional application No. 62/543,105, filed on Aug. 9, 2017.

(51) Int. Cl.
| | | |
|---|---|---|
| *C08J 3/09* | (2006.01) | |
| *B01F 17/00* | (2006.01) | |
| *C07C 67/02* | (2006.01) | |
| *C08L 39/08* | (2006.01) | |
| *C08L 71/02* | (2006.01) | |
| *C11D 11/00* | (2006.01) | |
| *C11C 3/10* | (2006.01) | |

(52) U.S. Cl.
CPC ........... *C08J 3/095* (2013.01); *B01F 17/0021* (2013.01); *B01F 17/0085* (2013.01); *C07C 67/02* (2013.01); *C08L 39/08* (2013.01); *C08L 71/02* (2013.01); *C08J 2339/08* (2013.01); *C08J 2471/02* (2013.01); *C08L 2201/56* (2013.01); *C11C 3/10* (2013.01); *C11D 11/0023* (2013.01)

(58) Field of Classification Search
CPC ........... C11D 10/00; C11C 3/10; C07C 67/02; C07C 67/03; B01F 17/0085; C08J 3/095; C08L 39/08
See application file for complete search history.

(56) References Cited

U.S. PATENT DOCUMENTS

| | | | |
|---|---|---|---|
| 6,156,833 A | 12/2000 | Rauls | |
| 6,187,382 B1 * | 2/2001 | Lightcap, Jr. | ........... C04B 40/04 427/384 |
| 6,372,697 B1 * | 4/2002 | Lorentz | ................. B60C 9/0007 508/198 |
| 6,495,074 B1 | 12/2002 | Carr | |
| 6,749,677 B2 | 6/2004 | Freisthler | |
| 2004/0248744 A1 * | 12/2004 | King | .................... C10M 169/04 508/437 |
| 2005/0249880 A1 | 11/2005 | Wallace et al. | |
| 2015/0267152 A1 * | 9/2015 | Matza | .................. C11D 3/2093 510/366 |
| 2016/0115425 A1 * | 4/2016 | Blankenburg | ....... B01D 17/047 554/20 |

OTHER PUBLICATIONS

Kuca, K. et al., Preparation of benzalkonium salts differing in the length of a side alkyl chain, 2007, Molecules, vol. 12, pp. 2341-2347 (Year: 2007).*
Invitation to Pay Additional Fees, and, where applicable, protest fee, from corresponding PCT Application No. PCT/US2018/046089.

* cited by examiner

*Primary Examiner* — Yate' K Cutliff
(74) *Attorney, Agent, or Firm* — Greer, Burns & Crain, Ltd.

(57) ABSTRACT

Emulsions for treating shingles, concrete, metallic substrates, mammalian skins, human hair or agricultural plants are described. The emulsions include soy alkyl and/or aryl ester; water; and a cationic surfactant to form the emulsion. Methods of using the emulsions are also described. Compositions including a modified oil alkyl and/or aryl ester comprising the transesterification reaction product of an oil and a surfactant having a hydroxyl group are described. Methods of using the compositions are also described. Methods of making a modified oil alkyl or aryl ester are described. The methods include transesterifying an oil with a surfactant having a hydroxyl group.

11 Claims, No Drawings

EMULSIFIED OILS

This application claims the benefit of U.S. Application Ser. No. 62/543,105, filed Aug. 9, 2017, entitled Emulsified Oils, which is incorporated herein by reference in its entirety.

BACKGROUND

Methods of treating a substrate to seal the surface and inhibit microbiological growth using a low VOC coating is known. For example, US 2005/0249880 describes a coating composition containing from about 30 wt % to about 50 wt % soy methyl ester emulsion, from about 15 wt % to about 25 wt % of a cationic acrylic resin polymer and from about 25 wt % to about 55 wt % of water. The coating is applied to architectural surfaces, such as masonry or concrete, and soft surfaces, such as wall coverings and currency, and allowed to cure. The coating composition resists microbiological growth in the liquid form and following curing.

Methods of restoring asphalt shingles are known. For example, U.S. Pat. No. 6,495,074 describes a method of maintaining and restoring weathered asphalt roofing shingles and strips. A re-saturant is applied to the shingles by spraying, rolling, or brushing. The restaurant includes fatty acid methyl esters, petroleum distillates, and water emulsions thereof. The emulsions are formed using non-ionic surfactants.

U.S. Pat. No. 6,749,677 describes a sealant for rejuvenating, sealing, and preserving asphalt pavement and concrete surfaces. The sealant composition includes soybean oil, alkyl esters of soybean oil, and at least one of d-limonene or other terpene hydrocarbons.

Methods of cleaning roof shingles are also known. One method involves applying a mixture of chlorine bleach and water to the roof for a period of time, such as 15 to 20 minutes, followed by rinsing with water. However, suitable precautions should be taken to protect the landscaping from damage by the bleach solution, and to protect the user.

U.S. Pat. No. 6,156,833 describes an emulsion base for non-aqueous chemical additives, and methods of making the emulsions. The emulsion comprises a mixture of 68-92% water, 0.1-0.2% 2-amino-2-methyl-1-propanol, 2.2-3.2% emulsifying surfactant blend, 10-20% soy methyl esters, and 0.25-0.5% of a 30% solution of polymer thickener.

Emulsions and other formulations stabilized by surfactants typically have other ingredients, such as thickeners, colorants, and the like. These additional ingredients are anionic in nature and would complex with cationic surfactants, thereby destabilizing the emulsion or formulation.

Therefore, there is a need for stabilized emulsions and other formulations containing surfactants. There is also a need for compositions which can clean and rejuvenate shingles and concrete.

DETAILED DESCRIPTION

Generally oils are emulsified in water with the help of emulsifiers (also known as surfactants).

One aspect of the invention is an emulsion. In one embodiment, the emulsion comprises soy alkyl ester, soy aryl ester, or mixtures of soy alkyl ester and soy aryl ester, water; and a cationic surfactant.

In some embodiments, the soy ester (alkyl and/or aryl) is present in an amount in the range of about 1 to about 80 wt %, or about 1 to about 70 wt %. In some embodiments, the cationic surfactant is present in an amount in the range of about 0.01 to about 20 wt %, or about 0.01 to about 10 wt %. In some embodiments, the water is present in an amount in the range of about 20 to about 95 wt %.

In some embodiments, the cationic surfactant comprises an alcohol ethoxylate sodium dodecyl sulfate, a benzalkonium salt, a polyquaternirium compound, poly(vinyl pyridine) co-N,N dimethyl ethyl methacrylate, or combinations thereof.

In some embodiments, the emulsion further comprises a solvent.

In some embodiments, the emulsion further comprises a triglyceride oil, paraffin oil, petroleum distillate, or combinations thereof.

Another aspect involves a method for treating shingles, concrete, metallic substrates, mammalian skins, human hair, or agricultural plants. In one embodiment, the method includes coating the shingles, concrete, metallic substrates, mammalian skins, human hair, or agricultural plants with an emulsion comprising: soy alkyl ester soy aryl ester, or combinations thereof; water; and a cationic surfactant to form the emulsion.

In some embodiments, the soy ester (alkyl and/or aryl) is present in an amount in the range of about 1 to about 80 wt %, or about 1 to about 70 wt %. In some embodiments, the surfactant is present in an amount in the range of about 0.01 to about 20 wt %, or about 0.01 to about 10 wt %. In some embodiments, the water is present in an amount in the range of about 20 to about 95 wt %.

In some embodiments, the cationic surfactant comprises benzalkonium salts, polyquaternirium compounds, and poly (vinyl pyridine) co-N,N dimethyl ethyl methacrylate, or combinations thereof.

In some embodiments, the emulsion further comprises a solvent.

In some embodiments, the emulsion further comprises a triglyceride oil, paraffin oil, petroleum distillate, or combinations thereof.

Another aspect involves a method of treating asphalt shingles, concrete, or metallic substrates, mammalian skins, human hair, or agricultural plants. In one embodiment, the method comprises coating the shingles, concrete, metallic substrates, mammalian skins, human hair, or agricultural plants with any of the compositions described above.

Another aspect involves a composition. In one embodiment, the composition includes a modified oil alkyl ester and/or modified oil aryl ester comprising the transesterification reaction product of an oil and a surfactant having a hydroxyl group.

In some embodiments, the surfactant comprises a cationic surfactant, an anionic surfactant, or a non-ionic surfactant.

In some embodiments, the surfactant comprises cationic surfactant. In some embodiments, the cationic surfactant comprises benzalkonium salts, polyquaternirium compounds, poly(vinyl pyridine) co-N,N dimethyl ethyl methacrylate, or combinations thereof.

In some embodiments, the surfactant comprises an anionic surfactant. In some embodiments, the anionic surfactant comprises sodium dodecyl sulfate, sodium lauryl benzene sulfonate, poly acrylic acid, anionic sulfate-based surfactants, and anionic sulfonate-based surfactants, or combinations thereof.

In some embodiments, the surfactant comprises a non-ionic surfactant. In some embodiments, the non-ionic surfactant comprises poly(ethylene oxide-b-propylene oxide), poly(ethylene oxide-b-butylene oxide), sorbitol esters of fatty acids, ethoxylated fatty alcohols, or combinations thereof.

In some embodiments, the composition further comprises water.

In some embodiments, the composition further comprises a solvent. In some embodiments, the solvent comprises methanol, ethanol, isopropanol, 2-ethyl hexanol, amyl alcohol, iso amyl alcohol, methyl lactate, ethyl lactate, methyl levulinate, ethyl levulinate, phenoxy ethanol, limonene, benzyl alcohol, methylene chloride, dimethyl formamide, dimethyl acetamide, N-methyl-2-pyrrolidinone, or combinations thereof.

In some embodiments, the oil comprises soybean oil, soybean oil methyl ester, epoxidized soybean oil, epoxidized soybean oil methyl ester, soybean oil cyclic carbonates, soybean oil methyl ester cyclic carbonates, maleated soybean oil, maleated soybean oil methyl ester, epoxidized and acrylated soybean oil, epoxidized and acrylated soybean oil methyl ester, silicone oils, algae oils and their epoxy, cyclic carbonate, maleated derivatives, or combinations thereof.

In some embodiments, the composition further comprises a triglyceride oil, paraffin oil, petroleum distillate, or combinations thereof.

Another aspect comprises a method of making the modified oil alkyl ester and/or aryl ester. In one embodiment, the method involves transesterifying the oil, such as a triglyceride oil, with a surfactant having a hydroxyl group. The surfactant is used as the alcohol to transesterify the oil. This results in the surfactant being incorporated into the modified oil ester. In this case, an emulsion is formed without the use of additional surfactants. In some embodiments, the modified oil ester can simply be mixed with water and applied. In some embodiments, the hydroxyl group may be on the end of the surfactant.

In some embodiments, the surfactant comprises a cationic surfactant, an anionic surfactant, or a non-ionic surfactant.

In some embodiments, the surfactant comprises cationic surfactant. In some embodiments, the cationic surfactant comprises benzalkonium salts, polyquaternirium compounds, and poly(vinyl pyridine) co-N,N dimethyl ethyl methacrylate, or combinations thereof.

In some embodiments, the surfactant comprises an anionic surfactant. In some embodiments, the anionic surfactant comprises sodium dodecyl sulfate, sodium lauryl benzene sulfonate, poly acrylic acid, anionic sulfate-based surfactants, and anionic sulfonate-based surfactants, or combinations thereof.

In some embodiments, the surfactant comprises a non-ionic surfactant. In some embodiments, the non-ionic surfactant comprises poly(ethylene oxide-b-propylene oxide), poly(ethylene oxide-b-butylene oxide), sorbitol esters of fatty acids, ethoxylated fatty alcohols, or combinations thereof.

In some embodiments, the composition further comprises water.

In some embodiments, the composition further comprises a solvent. In some embodiments, the solvent comprises methanol, ethanol, isopropanol, 2-ethyl hexanol, amyl alcohol, iso amyl alcohol, methyl lactate, ethyl lactate, methyl levulinate, ethyl levulinate, phenoxy ethanol, limonene, benzyl alcohol, methylene chloride, dimethyl formamide, dimethyl acetamide and N-methyl-2-pyrrolidinone, or combinations thereof.

In some embodiments, the oil comprises soybean oil, soybean oil methyl ester, epoxidized soybean oil, epoxidized soybean oil methyl ester, soybean oil cyclic carbonates, soybean oil methyl ester cyclic carbonates, maleated soybean oil, maleated soybean oil methyl ester, epoxidized and acrylated soybean oil, epoxidized and acrylated soybean oil methyl ester, silicone oils, algae oils and their epoxy, cyclic carbonate, and maleated derivatives, or combinations thereof.

Suitable soy alkyl esters and soy aryl esters include, but are not limited to, soy methyl ester, soy ethyl ester, soy propyl ester, soy isopropyl ester, soy 2-ethyl hexyl ester, soy amyl ester, soy isoamyl ester, soy phenyl ester, soy benzyl ester, or combinations thereof.

Examples of suitable triglyceride oils include, but are not limited to, soybean oil, soybean oil methyl ester, epoxidized soybean oil, epoxidized soybean oil methyl ester, soybean oil cyclic carbonates, soybean oil methyl ester cyclic carbonates, maleated soybean oil, maleated soybean oil methyl ester, epoxidized and acrylated soybean oil, epoxidized and acrylated soybean oil methyl ester, silicone oils, algae oils and their epoxy, cyclic carbonate, maleated derivatives, or combinations thereof. Paraffin oil, and/or petroleum distillate can optionally be included.

The surfactant can be a cationic surfactant, an anionic surfactant, or a non-ionic surfactant.

Examples of non-ionic surfactants include, but are not limited to, poly(ethylene oxide-b-propylene oxide), poly(ethylene oxide-b-butylene oxide), sorbitol esters of fatty acids, ethoxylated fatty alcohols, or combinations thereof.

Examples of anionic surfactants include, but are not limited to, sodium dodecyl sulfate, sodium lauryl benzene sulfonate, poly acrylic acid, or combinations thereof.

Examples of cationic surfactants include, but are not limited to, benzalkonium salts, polyquaternirium compounds, poly(vinyl pyridine) co-N,N dimethyl ethyl methacrylate, or combinations thereof. Some commercial examples are: ALGENE®, EMPIGEN® B series, BTC Onixide, and Quaterx 192.

The emulsion can optionally include a solvent. The solvent should be compatible with the modified oil alkyl and/or aryl ester or the soy alkyl and/or aryl ester and have the ability to clean a soiled surface. In some embodiments, the solvent is present in an amount in the range of about 1 to about 20 wt %. Examples of suitable solvents include, but are not limited to, methanol, ethanol, isopropanol, 2-ethyl hexanol, amyl alcohol, iso amyl alcohol, methyl lactate, ethyl lactate, methyl levulinate, ethyl levulinate, phenoxy ethanol, limonene, benzyl alcohol, methylene chloride, dimethyl formamide, dimethyl acetamide and N-methyl-2-pyrrolidinone, or combinations thereof. In some embodiments, the solvent is a polar solvent. Suitable polar solvents include, but are not limited to, methanol, ethanol, isopropanol, 2-ethyl hexanol, phenoxy ethanol, or combinations thereof.

The emulsion can optionally include one or more of conventional additives, such as thickeners, and preservatives. The preservative can be present in the range of about 0.01 wt % to about 10 wt %. The thickener can be present in the range of about 0.01 wt % to about 5 wt %

The use of cationic surfactants may also provide functions in addition to the emulsification of oil. Multifunctionality is exemplified by, but not limited to, cleaning/penetrating surfaces, UV protection, antimicrobial, biofilm control, control algal and fungal growth, solar reflective, or combinations thereof.

Surfaces includes but not limited to concrete, asphalt shingles, hard surfaces such as wood, metals, plastic and composites, soft surfaces such as leaves, skins and fabrics The emulsion or modified oil alkyl ester and/or aryl ester produced from the methods can be used as a carrier for solvents, pigments, additives such as biocides, pesticides, weedicides, cosmetics, and drugs. The emulsion or modified oil alkyl ester and/or aryl ester produced from the methods can be used to clean and rejuvenate shingles, concrete, and metals. It can be used to apply biocides, pesticides, and weedicides to plants. The emulsion or modified oil alkyl ester and/or aryl ester produced from the methods can be used to replace coal tar emulsions and petroleum distillates in cosmetics, shampoos, and other hair treatments. It can also be used in drug delivery.

The invention is further described with the following examples and should not be construed to limit the scope of the invention.

EXAMPLES

The ingredients mentioned in the examples falls under specific classification but may be available from different manufacturers. The classification of ingredients and their manufacturer or supplier is provided in the following table.

| Ingredients | Generic Classification | Manufacturer/Supplier |
|---|---|---|
| Altox 4912 | Non ionic surfactant | Croda |
| Break-Thru EMV 20 | Defoamer | Evonik |
| Carboset | Acrylic emulsion | Lubrizol |
| Cationic Starch | Thickening agent | ADM |
| Ethanol | Solvent | Aldrich Chemicals |
| Hexadecyltrimethylammonium bromide | Cationic Surfactant | Aldrich Chemicals |
| Isopropanol | Solvent | Aldrich Chemicals |
| Sodium dodecyl sulfate (SDS) | Anionic Surfactant | Aldrich Chemicals |
| Solagum SH-210 | Thickening agent | Seppic |
| Soybean oil methyl ester or Methyl soyate | Biodiesel | Chempoint |
| Tamadol 9 1-6 | Non ionic surfactant | Evonik |
| Tween 80 | Non-ionic surfactant | Aldrich Chemicals |
| Xanthan gum | Thickening agent | CPKelco |

Control Example 1

In an emulsion kettle containing 10.8 liters of water, 135 g each of Break-Thru, Tween-80, Altox 4912 and 270 g of Carboset were added. The contents were mixed at 300 rpm and 6.75 kg of methyl soyate was added slowly over a period of one hour. The contents were mixed well for additional 3 hours. The process did not produce emulsified soy methyl ester.

Example 1

10.8 liters of water, 135 g each of Break-Thru, Tween-80, Altox 4912, and 270 g of Carboset were mixed in a separate container. The solution obtained was slowly added to 6.75 kg of methyl soyate in an emulsion kettle over a period of one hour with a stirring speed 300 rpm. The contents were mixed well for an additional 3 hours. The process produced emulsions that were stable up to a week.

Example 2

10.8 liters of water, 1.35 l ethanol, 135 g each of Break-Thro, Tween-80, Altox 4912, and 270 g of Carboset were mixed in a separate container. The solution obtained was slowly added to 6.75 kg of methyl soyate in an emulsion kettle over a period of one hour with a stirring speed 300 rpm. The contents were mixed well for an additional 3 hours. The process produced emulsions that were stable up to 30 days.

Example 3

3 g of sodium dodecyl sulfate and 63 mL of water were mixed in a separate container. This mixture was added to 237 g of SME emulsion obtained from Example 2 to produce emulsions that were stable up to three months.

Example 4

1.2 liters of water, 47.8 g each of Break-Thru, Tween-80, Altox 4912, 85.4 gram sodium dodecyl sulfate, and 47 mL of denatured ethanol were mixed in a separate container. The solution obtained was slowly added to 2.4 kg of methyl soyate in an emulsion kettle over a period of one hour with a stirring speed 300 rpm. The contents were mixed well for an additional 3 hours. The process produced emulsions that were stable for more than three months.

Example 5

0.3 grams xanthan gum and 10 gram soy methyl ester were mixed in a container. The mixture was added to a solution comprises of 89.2 grams of water and 0.5 gram of sodium dodecyl sulfate and stirred at 300 rpm for 30 min. The process produced emulsions that were stable up to two weeks.

Example 6

0.3 grams xanthan gum and 10 gram soy methyl ester were mixed in a container. The mixture was added to a solution comprises of 89 grams of water, 0.5 gram of sodium dodecyl sulfate, 0.1 gram potassium sorbate, 0.1 gram sodium benzoate and stirred at 300 rpm for 30 min. The process produced emulsions that were stable up to two weeks.

Example 7

0.3 grams xanthan gum, 7 gram soy methyl ester, and 3 grams of soybean oil were mixed in a container. The mixture was added to a solution comprising 89 grams of water, 0.5 gram of sodium dodecyl sulfate, 0.1 gram potassium sorbate, and 0.1 gram sodium benzoate and stirred at 300 rpm for 30 min. The process produced emulsions that were stable up to two weeks.

Example 8

1.24 lb of xanthan gum, 5 gallons of soy methyl ester, and 2.5 gallons of limonene were mixed in a 10 gallon bucket. The mixture was added to 100 gallon drum that comprises of a solution made from 42.5 gallons of water, 2.07 lb of sodium dodecyl sulfate, 0.41 lb of potassium sorbate, and 0.41 lb of sodium benzoate and stirred at 300 rpm for 1 hour. The process produced emulsions that were stable up to three months.

Example 9

2.48 lb of xanthan gum, 5 gallons of soy methyl ester, and 2.5 gallons of limonene were mixed in a 10 gallon bucket.

The mixture was added to 100 gallon drum that comprises of a solution made from 42.5 gallons of water, 5 lb of sodium dodecyl sulfate, 0.5 lb of potassium sorbate, and 0.5 lb of sodium benzoate and stirred at 300 rpm for 1 hour. The process produced emulsions that were stable up to three months.

Example 10

5 gallons of soy methyl ester was added to a 100 gallon drum that comprises of a solution made from 45 gallons of water and 0.21 lb of Tamadol 91-6 and stirred at 300 rpm for 1 hour. Added 0.42 lb of Solagum SH-210 and continued mixing for 1 hour. The process produced emulsions that were stable up to one year.

Example 11

5 gallons of soy methyl ester was added to a 100 gallon drum that comprises of a solution made from 45 gallons of water and 0.21 lb of Tamadol 91-6 and stirred at 300 rpm for 1 hour. Added 0.42 lb of Solagum SH-210, 5 gallons of limonene and continued mixing for 1 hour. The process produced emulsions that were stable up to one year.

Example 12

0.3 grams cationic starch, 7 gram soy methyl ester, and 3 grams of soybean oil were mixed in a container. The mixture was added to a solution comprising 89 grams of water, and 0.7 gram of hexadecyltrimethylammonium bromide and stirred at 300 rpm for 30 min. The process produced emulsions that were stable up to two weeks.

Example 13: Process for Making SME Emulsion

In the first step, 1.5 g of poly(N,N-dimethylamino ethyl methacrylate-co-stearyl methacrylate) was mixed with 10 g of Soygold 1100 (Available from Chempoint) in a 50 mL beaker.

In the second step, 1.5 g of hexadecyltrimethylammonium bromide was weighed in a 250 mL beaker, and 78 mL tap water was added and mixed well on a magnetic stir plate. Once a solution was formed, 5 g of citric acid was added and stirred well to form a homogenous clear solution. To this solution, the product obtained from step 1 was added and mixed well for 30 min to obtain an emulsion which is stable for more than 24 hours.

Control Example 14

1.5 grams of hexadecyltrimethylammonium bromide was weighed in a 250 mL beaker, and 88.5 mL tap water was added and mixed well on a magnetic stir plate. Once a solution was formed, 10 g of Soygold 1100 was added and mixed well for 30 min. The product obtained separates into two layers within 30 min.

Control Example 15

1.5 g of hexadecyltrimethylammonium bromide was weighed in a 250 mL beaker, and 83.5 mL tap water was added and mixed well on a magnetic stir plate. Once a solution was formed, 5 g of citric acid was added and stirred well to form a homogenous clear solution. To this solution, 10 g of Soygold 1100 was added and mixed well for 30 min. The product obtained separates into two layers within 30 min.

Example 16

In the first step, 1 part of N,N-dimethylamino ethyl methacrylate, 0.1 part of mercapto ethanol, 0.1 part of azobisisobutyro nitrile, and 3 parts of soybean oil is mixed in a reaction kettle equipped with a stirrer, thermocouple, inert gas feeder and a reflux condenser. The reactor is heated to 60° C. under argon gas, and the temperature is maintained for 12 hours. To the reaction mass, 3 parts of citric acid is added and heated up to 120° C. for 6 hours, then is cooled to room temperature to obtain product 1.

In the second step, 0.1 part of hexadecyltrimethylammonium bromide is weighed in a beaker, and 8 parts of tap water is added and mixed well on a magnetic stir plate. Once a solution is formed, 1.9 parts of the product obtained from step 1 is added and mixed well for 30 min to obtain an emulsion which is stable for more than 24 hours.

An idealized representation of this example is shown below.

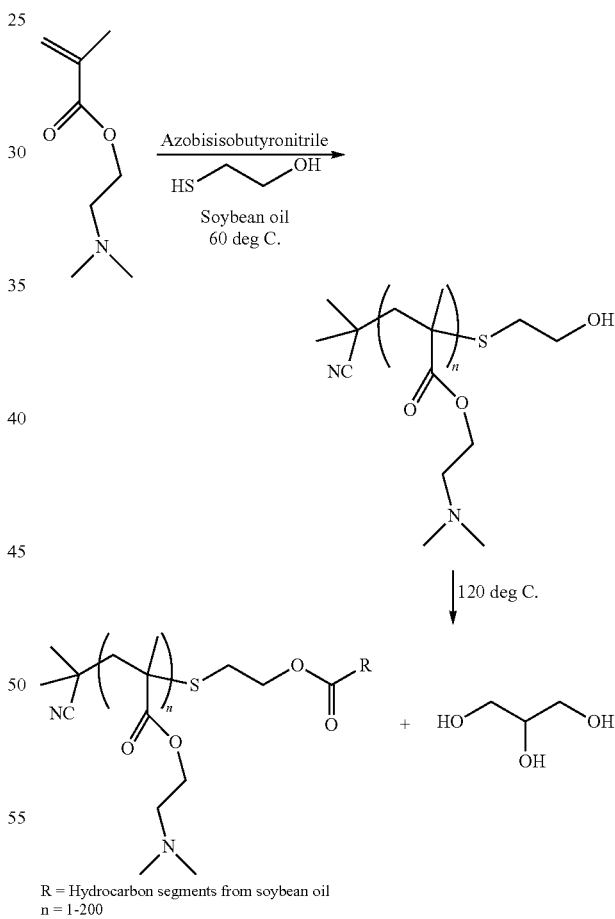

R = Hydrocarbon segments from soybean oil
n = 1-200

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A composition comprising:
a cationic modified oil alkyl ester, modified oil aryl ester, or combinations thereof, the cationic modified oil alkyl ester or modified oil aryl ester comprising a neutralized transesterification reaction product of an oil and a poly(N,N dimethyl ethyl methacrylate) having a hydroxyl group.

2. The composition of claim 1 wherein the poly(N,N dimethyl ethyl methacrylate) comprises a poly(vinyl pyridine) co-N,N dimethyl ethyl methacrylate.

3. The composition of claim 1 further comprising water.

4. The composition of claim 1 further comprising a solvent.

5. The composition of claim 4 wherein the solvent comprises methanol, ethanol, isopropanol, 2-ethyl hexanol, amyl alcohol, iso amyl alcohol, methyl lactate, ethyl lactate, methyl levulinate, ethyl levulinate, phenoxy ethanol, limonene, benzyl alcohol, methylene chloride, dimethyl formamide, dimethyl acetamide, N-methyl-2-pyrrolidinone, or combinations thereof.

6. The composition of claim 1 wherein the oil comprises soybean oil, soybean oil methyl ester, epoxidized soybean oil, epoxidized soybean oil methyl ester, soybean oil cyclic carbonates, a soybean oil methyl ester cyclic carbonate, maleated soybean oil, maleated soybean oil methyl ester, epoxidized and acrylated soybean oil, epoxidized and acrylated soybean oil methyl ester, a silicone oil, an algae oil, an epoxized algae oil, an algae oil cyclic carbonate, a maleated algae oil, or combinations thereof.

7. The composition of claim 1 further comprising a triglyceride oil, a paraffin oil, a petroleum distillate, or combinations thereof.

8. A method of making a cationic modified oil alkyl ester or modified oil aryl ester comprising:
transesterifying an oil with a poly(N,N dimethyl ethyl methacrylate) having a hydroxyl group to form a transesterification reaction product; and
neutralizing the transesterification reaction product.

9. The method of claim 8 wherein the a poly(N,N dimethyl ethyl methacrylate) comprises a poly(vinyl pyridine) co-N,N dimethyl ethyl methacrylate.

10. The method of claim 8 wherein the oil comprises soybean oil, soybean oil methyl ester, epoxidized soybean oil, epoxidized soybean oil methyl ester, soybean oil cyclic carbonates, soybean oil methyl ester cyclic carbonates, maleated soybean oil, maleated soybean oil methyl ester, an epoxidized and acrylated soybean oil, an epoxidized and acrylated soybean oil methyl ester, a silicone oil, an algae oil, an epoxidized algae oil, an algae oil cyclic carbonate, a maleated algae oil, or combinations thereof.

11. The composition of claim 1 wherein the oil is a triglyceride oil.

* * * * *